US008377947B2

(12) United States Patent
Chen

(10) Patent No.: US 8,377,947 B2
(45) Date of Patent: Feb. 19, 2013

(54) TREATING ALZHEIMER'S DISEASE AND OSTEOPOROSIS AND REDUCING AGING

(76) Inventor: Chien-Hung Chen, Forest Hills, NY (US)

( * ) Notice: Subject to any disclaimer, the term of this patent is extended or adjusted under 35 U.S.C. 154(b) by 248 days.

(21) Appl. No.: 12/723,771

(22) Filed: Mar. 15, 2010

(65) Prior Publication Data

US 2010/0234295 A1 Sep. 16, 2010

Related U.S. Application Data

(60) Provisional application No. 61/160,533, filed on Mar. 16, 2009.

(51) Int. Cl.
*A61K 31/52* (2006.01)
*A61K 31/60* (2006.01)
*A61K 31/19* (2006.01)
*A61K 31/18* (2006.01)
*A61K 33/02* (2006.01)
*A61K 31/14* (2006.01)

(52) U.S. Cl. ............... 514/263.21; 514/165; 514/415; 514/420; 514/563; 514/570; 514/605; 514/630; 514/635; 514/646

(58) Field of Classification Search ............... 514/440, 514/635, 263.21, 165, 415, 420, 563, 570, 514/605, 630, 646
See application file for complete search history.

(56) References Cited

U.S. PATENT DOCUMENTS

| | | | |
|---|---|---|---|
| 5,100,919 A | 3/1992 | Ulrich | |
| 5,385,915 A | 1/1995 | Bauxbaum | |
| 5,597,826 A * | 1/1997 | Howard et al. ........... | 514/252.14 |
| 5,721,345 A | 2/1998 | Roberfroid et al. | |
| 5,776,431 A * | 7/1998 | Galat .............................. | 424/44 |
| 5,840,719 A | 11/1998 | Rubin | |
| 6,589,944 B1 | 7/2003 | Rahbar | |
| 6,693,106 B2 * | 2/2004 | Rahbar et al. ............ | 514/263.34 |
| 6,927,223 B1 | 8/2005 | Meadows et al. | |
| 7,329,638 B2 | 2/2008 | Yang et al. | |
| 2002/0040063 A1 | 4/2002 | Chandran et al. | |
| 2002/0045621 A1 | 4/2002 | Reiner et al. | |
| 2002/0137787 A1 | 9/2002 | Geho et al. | |
| 2002/0173511 A1 | 11/2002 | Wurtman et al. | |
| 2004/0053900 A1 | 3/2004 | Masferrer | |
| 2004/0132758 A1 | 7/2004 | Vaccaro et al. | |
| 2004/0167114 A1 | 8/2004 | Fliss | |
| 2005/0054731 A1 | 3/2005 | Folli et al. | |
| 2005/0080074 A1 | 4/2005 | Wacker et al. | |
| 2005/0187267 A1 | 8/2005 | Hamann et al. | |
| 2006/0040980 A1 | 2/2006 | Lind et al. | |
| 2006/0069161 A1 | 3/2006 | Lee et al. | |
| 2006/0134206 A1 | 6/2006 | Lyer et al. | |
| 2006/0147947 A1 | 7/2006 | Apfeld et al. | |
| 2006/0276416 A1 | 12/2006 | Sinclair et al. | |
| 2007/0015839 A1 | 1/2007 | Folli et al. | |
| 2007/0105790 A1 | 5/2007 | Khodadoust et al. | |
| 2007/0142291 A1 | 6/2007 | Lin | |
| 2007/0149466 A1 | 6/2007 | Milburn et al. | |
| 2007/0161543 A1 | 7/2007 | Yu et al. | |
| 2007/0191351 A1 | 8/2007 | Cowen et al. | |
| 2007/0249583 A1 | 10/2007 | Stein et al. | |
| 2009/0286760 A1 | 11/2009 | Chen et al. | |

FOREIGN PATENT DOCUMENTS

| | | |
|---|---|---|
| WO | WO01/82926 | 11/2001 |
| WO | 2004/078113 | 9/2004 |
| WO | 2005/025673 | 3/2005 |
| WO | WO2005/023202 | 3/2005 |
| WO | WO2006/024491 | 3/2006 |
| WO | 2006/078698 | 7/2006 |
| WO | WO2007/080124 | 7/2007 |

OTHER PUBLICATIONS

Carruba, M. O. et al., "Effects of Dextrofenfluramine and Other Anorectic Drugs on Experimentally Induced Hyperphagias", Adv. Biosci., 60: 353-360 (1986).
Dowling et al., "Metformin Inhibits Mammalian Target of Rapamycin-Dependent Translation Initiation in Breast Cancer Cells", Cancer Res, 67: 10804-10812, Nov. 15, 2007.
Harris et al., "Chemoprevention of Breast Cancer in Rats by Celecoxib, a Cyclooxygenase 2 Inhibitor", Cancer Research, 60, 2101-2103, Apr. 15, 2000.
Krejs, G. J., "Metabolic Benefits Associated with Sibutramine Therapy", Int. J. Obesity 26 (Suppl. 4); 534-537 (2002.
Prete et al., Physiology & Behavior, 36 (5): 685-689, 1999.
Hu et al., "Inhibition of COX-2 by celecoxib enhances glucocorticoid receptor function", Mol. Psychiatry, May 2005, 10(5): 426-28.
International Preliminary Report on Patentability issued from International Application No. PCT/US2009/044362 mailed on Nov. 25, 2010.
Barnes Christopher J. et al: "Aspirin, but not sodium salicylate, indomethacin, or nabumetone, reversibly suppresses 1,2-dimethylhydrazine-induced colonic aberrant crypt foci in rats", Digestive Diseases and Sciences, vol. 42, No. 5, 1997, pp. 920-926, ISSN: 0163-2116 (abstract only).
Beckman, "Great Balls of Fat", Science, Mar. 3, 2006, vol. 311.
Buhl, et al. "*Long-Term AICAR Administration Reduces Metabolic Disturbances and Lowers Blood Presure in Rats Displaying Features of the Insulin Resistance Syndrome*", Diabetes, vol. 51, Jul. 2002.
Daval, et al., "*Anti-lipolytic Action of AMP-activated protein Kinase in Rodent Adipocytes*", The Journal of Biological Chemistry, vol. 280, No. 28, Issue of Jul. 1, pp. 25250-25257, 2005.

(Continued)

*Primary Examiner* — Jennifer M Kim
(74) *Attorney, Agent, or Firm* — Fish & Richardson P.C.

(57) ABSTRACT

Use of a composition for treating Alzheimer's disease, osteoporosis, sleep apnea, erectile dysfunction, McArdle disease, or a carbohydrate metabolism disorder, or for reducing aging or fatigue. The composition includes a first agent selected from the group consisting of an oxidative phosphorylation inhibitor, an ionophore, and an adenosine 5'-monophosphate-activated protein kinase activator; a second agent that possesses anti-inflammatory activity; and a third agent that possesses serotonin activity.

18 Claims, No Drawings

OTHER PUBLICATIONS

Extended Search Report issued on Oct. 14, 2009 in European Application No. 09160525.3.

Fonseca: Clinical cornerstone, 7(2/3):61:72, 2005.

Greco et al, "Leptin regulates Tau phosphorylation and Amyloid through AMPK in Neuronal Cells", Biochem Biophys Res Commun., Feb. 27, 2009; vol. 380(1): 98-104.

He, et al., "*Calyculin and okadaic acid promote perilipin phosphorylation and increase lipolysis in primary rat adipocytes*", Biochimica et Biophysica Acta 1761 (2006) 247-255.

International Preliminary Report on Patentability issued in international application PCT/US2008/051123, date of mailing Jul. 30, 2009.

International Search Report and Written Opinion issued in corresponding international application PCT/US09/44362, Jun. 19, 2009.

International Search Report from International Application No. PCT/US10/27330 mailed May 6, 2010.

Kemp, et al. "*AMP-activated protein kinase, super metabolic regulator*", 2003 Biochemical Society, pp. 162-168.

Knowler, et al., "*Reduction in the Incidence of type 2 Diabetes with Lifestyle Intervention or Metformin*", N Engl J. Med. vol. 346, No. 6: Feb. 7, 2002: 393-403.

Merrill, et al., "*Influence of malonyl-CoA and palmitate concentration on rate of palmitate oxidation in rate muscle*", J. App Physiol. Nov. 1998: 85(5) :1909-14.

Muldoon, et al.: J. Clin. Endocrinology & Metabolism, 89(1):266-271, 2004.

Ruderman, et al., "*Amp Kinase and Malonyl-COA: Targets for Therapy of the Metabolic Syndrome*", Nat. Rev. Drug Discovery, vol. 3, Apr. 2004, 340-51.

Saha, et al., "*Activation of Malonyl-CoA Decarboxylase in Rat Skeletal Muscle by Contraction and the AMP-activated Protein Kinase Activator 5-Aminoimidazole-4-carboxamide-I-B-d-ribofuranoside*", J. Bio. Chem., vol. 275, No. 32, Issue of Aug. 11, pp. 24279-24283, 2000.

Sudlow et al., "Cyclic AMP Levels, Adenylyl Cyclase Activity, and Their Stimulation by Serotonin Quantified In Intact Neurons", J Gen Physiol., 1997, vol. 110(3), pp. 243-255; p. 244, col. 1, last para: 5-HT (serotonin creatinine sulfate complex; Sigma Chemical Co.).

Suzuki Kaon et al: "Metformin suppresses the colorectal carcinogenesis via activating AMP protein kinase in the mouse model", Gastroenterology, vol. 134, No. 4, Suppl. 1, Apr. 2008, p. A630 (abstract only).

Yu H-G et al. "The effects of acetylsalicylic acid on proliferation, apoptosis, and invasion of cyclooxygenase-2 negative colon cancer cells", European Journal of Clinical Investigation, vol. 32, No. 11, Nov. 2002, pp. 838-846 (abstract only).

Zakikhani Mahvash et al. "Metformin is an AMP kinase-dependent growth inhibitor for breast cancer cells", Cancer Research, vol. 66, No. 21, Nov. 1, 2006, pp. 10269-10273.

Zhang, et al., "*Tumor Necrosis Factor-a Stimulates Lipolysis in Differentiated Human Adipocytes Through Activation of Extraceullar Signal-related Kinase and Elevation of Intraceullar cAMP*", Diabetes, vol. 51, Oct. 2002.

Zhou, et al., "*Role of AMP-activated protein kinase in mechanism of metformin action*", The Journal of Clinical Investigation, vol. 108, No. 8, Oct. 2001: 1167-1174.

\* cited by examiner

TREATING ALZHEIMER'S DISEASE AND OSTEOPOROSIS AND REDUCING AGING

CROSS REFERENCE TO RELATED APPLICATION

Pursuant to 35 U.S.C. §119(e), this application claims priority to U.S. Provisional Application Ser. No. 61/160,533, filed Mar. 16, 2009, the contents of which are hereby incorporated by reference.

BACKGROUND

Alzheimer's disease is an age-related neurological disease characterized by memory loss and dementia. Osteoporosis, also an age-related disease, results in low bone mass and loss of bone tissue. There is a need to develop a new approach to treat these two age-related diseases or otherwise reduce aging.

SUMMARY

In one aspect, the present invention features a method for treating Alzheimer's disease or osteoporosis by administering to a subject in need of the treatment a composition that includes (1) a first agent that can be an oxidative phosphorylation inhibitor, an ionophore, or an adenosine 5'-monophosphate-activated protein kinase (AMPK) activator, (2) a second agent that possesses anti-inflammatory activity, and (3) a third agent that possesses or maintains serotonin activity. The term "oxidative phosphorylation inhibitor" refers to a suitable agent that inhibits oxidative phosphorylation, such as oxidative phosphorylation uncouplers. An ionophore is a lipid-soluble molecule capable of transporting an ion across the lipid bilayer of cell membranes. An AMPK activator is an agent that activates AMPK to phosphorylate its substrates, e.g., acetyl-CoA carboxylase and malonyl-CoA decarboxylase. Examples of the first agent include metformin (e.g., metformin chloride), phenformin, buformin, ephedrine, thyroxine, salicylanilide, and salicylic acid. The second agent can be a suitable anti-inflammatory compound (e.g., non-steroidal anti-inflammatory compound). Examples include aspirin, diclofenac (e.g., diclofenac potassium or diclofenac sodium), ibuprofen (e.g., dexibuprofen or dexibuprofen lysine), indomethacin, acetaminophen, nimesulide, and a COX-2 inhibitor (e.g., a nitric oxide-based COX-2 inhibitor). The third agent can be a compound possessing or maintaining at least one of serotonin's activities and, when used in combination with the first and second agents, effectively treats one or more of the target diseases of this invention. Examples include serotonin (e.g., serotonin sulfate, a serotonin creatinine sulfate complex, or serotonin hydrochloride) and a serotonin re-uptake inhibitor. A preferred composition contains metformin hydrochloride, aspirin, and a serotonin creatinine sulfate complex. The three agents mentioned above can treat a target disease via biological mechanisms other than those described therein. For example, metformin may treat a target disease (e.g., osteoporosis) via a mechanism other than inhibiting oxidative phosphorylation or activating AMPK.

The composition described above can contain 5-5,000 mg (e.g., 5-3,000 mg, 5-1,500 mg, or 5-1,000 mg) of the first agent, 1-5,000 mg (e.g., 1-3,000 mg, 1-1,000 mg, 1-500 mg, or 1-100 mg) of the second agent, and 0.1-1,000 mg (e.g., 0.1-100 mg, 0.1-50 mg, or 0.1-30 mg) of the third agent, or in quantities of the same ratio as that calculated based on the above amounts.

In another aspect, the present invention features a method for reducing aging or fatigue by administering the above-described composition to a subject in need of the treatment.

In yet another aspect, this invention features a method for treating sleep apnea, erectile dysfunction, McArdle disease, or a carbohydrate metabolism disorder by administering the above-described composition to a subject in need of the treatment.

Also within the scope of this invention is the use of the above-described composition for the manufacture of a medicament for any of the diseases and disorders mentioned above.

The details of one or more embodiments of the invention are set forth in the description below. Other features, objects, and advantages of the invention will be apparent from the description and from the claims.

DETAILED DESCRIPTION

Disclosed herein is use of a composition for treating various diseases/disorders, e.g., Alzheimer's disease, osteoporosis, sleep apnea, erectile dysfunction, McArdle disease, or a carbohydrate metabolism disorder, or for reducing aging or fatigue. The composition includes at least three active agents which are described immediately below and also in U.S. Patent Application Nos. 60/885,212 and 12/014,932.

The first agent can be an oxidative phosphorylation inhibitor, an ionophore, or an adenosine 5'-monophosphate-activated protein kinase (AMPK) activator. The first agent can include, in addition to those described above, 4,6-dinitro-o-cresol, uncoupling proteins (e.g., UCP1, UCP2, or UCP3), carbonyl cyanide p-(trifluoromethoxy)phenyl-hydrazone, carbonyl cyanide m-chlorophenyl-hydrazone, C5 gene products, dinitrophenol (e.g., 2,4-dinitrophenol), efrapeptin (A23871), guanethidine, chlorpromazine, amytal, secobarbital, rotenone, progesterone, antimycin A, naphthoquinone, 8-hydroxyquinoline, carbon monoxide, cyanides, azides (e.g., $NaN_3$), dicoumarin, bilirubin, bile pigment, ephedrine, hydrogen sulfide, tetraiodothyronine, quercetin, 2,4-bis(p-chloroanilino)pyrimidine, glyceraldehyde-3-phosphate dehydrogenase, oligomycin, tributyltin chloride, aurovertin, rutamycin, venturicidin, mercurials, dicyclohexylcarbdiimide, Dio-9, m-chlorophenyl-hydrazone mesoxalonitrile, ionomycin, calcium ionophores (e.g., A23187, NMDA, CA 1001, or enniatin B), compounds that increase the $Ca^{+2}$ concentration in mitochondria (e.g., atractyloside, bongkrekic acid, thapsigargin, amino acid neurotransmitters, glutamate, N-methyl-D-aspartic acid, carbachol, ionophores, inducers of potassium depolarization), apoptogens (i.e., compounds that induce apoptosis), valinomycin, gramicidin, nonactin, nigericin, lasalocid, and monensin. The first agent can be an AMPK activator (e.g., metfomin or phenformin, buformin, 5'-aminoimidazole-4-carboxyamide-ribonucleoside, thienopyridones, resveratrol, nootkatone, thiazole, or adiponectin).

The second agent can include steroidal anti-inflammatory drugs and non-steroidal anti-inflammatory drugs. Examples of steroidal anti-inflammatory drugs include glucocorticoids, hydrocortisone, cortisone, beclomethasone, dipropionate, betamethasone, dexamethasone, prednisone, methylprednisolone, triamcinolone, fluocinolone acetonide, fludrocortisone, and beclometasone propionate. Examples of non-steroidal anti-inflammatory drugs (NSAIDs) include A183827, ABT963, aceclofenac, acemetacin, acetyl salicylic acid, AHR10037, alclofenac, alminoprofen, ampiroxicam, amtolmetin guacil, apazone, atliprofen methyl ester, AU8001, benoxaprofen, benzydamine flufenamate, bermoprofen, bezpiperylon, BF388, BF389, BIRL790, BMS347070, bromfenac, bucloxic acid, butibufen, BW755C, C53, C73, C85, carprofen, CBS1108, celecoxib, CHF2003, chlorobiphenyl, choline magnesium trisalicylate, CHX108, cimicoxib, cinnoxicam, clidanac, CLX1205, COX-2 inhibitors, CP331, CS502, CS706, D1367, darbufelone, deracoxib, dexketoprofen, DFP, DFU, diflunisal, DP155, DRF4367, E5110, E6087, eltenac, ER34122, esflurbiprofen, etoricoxib, F025, felbinac ethyl, fenbufen, fenclofenac, fenclozic acid, fenclozine, fenoprofen, fentiazac, feprazone, filenadol, flobufen, florifenine, flosulide, flubichin methanesulfonate, flufenamic acid, fluprofen, flurbiprofen, FPL62064, FR122047, FR123826, FR140423, FR188582, FS205397, furofenac, GR253035, GW406381, HAI105, HAI106, HCT2035, HCT6015, HGP12, HN3392, HP977, HX0835, HYAL AT2101, ibufenac, ibuproxam-beta-cyclodextrin, icodulinum, IDEA070, iguratimod, imrecoxib, indoprofen, IP751, isoxepac, isoxicam, KC764, ketoprofen, L652343, L745337, L748731, L752860, L761066, L768277, L776967, L783003, L784520, L791456, L804600, L818571, LAS33815, LAS34475, licofelone, LM 4108, lobuprofen, lornoxicam, lumiracoxib, mabuprofen, meclofenamic acid, meclofenamate sodium, mefenamic acid, meloxicam, mercaptoethylguanidine, mesoporphyrin, metoxibutropate, miroprofen, mofebutazone, mofezolac, MX1094, nabumetone, naproxen sodium, naproxen-sodium/metoclopramide, NCX1101, NCX284, NCX285, NCX4016, NCX4215, NCX530, niflumic acid, nitric oxide-based NSAIDs (NitroMed, Lexington, Mass.), nitrofenac, nitroflurbiprofen, nitronaproxen, NS398, ocimum sanctum oil, ONO3144, orpanoxin, oxaprozin, oxindanac, oxpinac, oxycodone/ibuprofen, oxyphenbutazone, P10294, P54, P8892, pamicogrel, parcetasal, parecoxib, PD138387, PD145246, PD164387, pelubiprofen, pemedolac, phenylbutazone, pirazolac, piroxicam, piroxicam beta-cyclodextrin, piroxicam pivalate, pirprofen, pranoprofen, resveratrol, R-ketoprofen, R-ketorolac, rofecoxib, RP66364, RU43526, RU54808, RWJ63556, S19812, S2474, S33516, salicylsalicylic acid, satigrel, SC236, SC57666, SC58125, SC58451, SFPP, SKF105809, SKF86002, sodium salicylate, sudoxicam, sulfasalazine, sulindac, suprofen, SVT2016, T3788, TA60, talmetacin, talniflumate, tazofelone, tebufelone, tenidap, tenoxican, tepoxalin, tiaprofenic acid, tilmacoxib, tilnoprofen arbamel, tinoridine, tiopinac, tioxaprofen, tolfenamic acid, tolmetin, triflusal, tropesin, TY10222, TY10246, TY10474, UR8962, ursolic acid, valdecoxib, WAY120739, WY28342, WY41770, ximoprofen, YS 134, zaltoprofen, zidometacin, and zomepirac.

The third agent includes serotonin and its functional equivalents. The functional equivalents of serotonin include serotonin metabolites (e.g., 5-hydroxyindoleacetic acid), serotonin transporter inhibitors (e.g., paroxetine, fluoxetine, fenfluramine, fluvoxamine, sertraline, imipramine, and those disclosed in WO 03/00663), serotonin receptor 2c modulators (e.g., BVT933, DPCA37215, IK264, PNU22394, WAY161503, R-1065, YM348, and those disclosed in U.S. Pat. No. 3,914,250, WO 01/66548, WO 02/10169, WO 02/36596, WO 02/40456, WO 02/40457, WO 02/44152, WO 02/48124, WO 02/51844, and WO 03/033479), serotonin reuptake inhibitors (e.g., arylpyrrolidine compounds, phenylpiperazine compounds, benzylpiperidine compounds, piperidine compounds, tricyclic gamma-carbolines duloxetine compounds, pyrazinoquinoxaline compounds, pyridoindole compounds, piperidyindole compounds, milnacipran, citalopram, sertraline metabolite desmethylsertraline, norfluoxetine, citalopram metabolite desmethylcitalopram, escitalopram, d,l-fenfluramine, femoxetine, ifoxetine, cyanodothiepin, litoxetine, dapoxetine, nefazodone, cericlamine, trazodone, mirtazapine, fluoxetine, fluvoxamine, indalpine, indeloxazine, milnacipran, paroxetine, sertraline, sibutramine, zimeldine, trazodone hydrochloride, dexfenfluramine, and those disclosed in U.S. Pat. No. 6,365, 633, WO 01/27060, and WO 01/162341), serotonin and noradrenaline reuptake inhibitors (e.g., venlafaxine, venlafaxine metabolite O-desmethylvenlafaxine, clomipramine, and clomipramine metabolite desmethylclomipramine), serotonin 1A receptor antagonists (e.g., arylpiperazine compounds, azaheterocyclylmethyl derivatives of heterocycle-fused benzodioxans, or buspirone), serotonin 2A receptor antagonists (e.g., MDL100907 and fananserin), serotonin 2B or 2C receptor antagonists (e.g., pirazino(aza)indole compounds or serotonergic compounds), serotonin 6 receptor antagonists (e.g., 5-halo-tryptamine compounds), serotonin 7 receptor antagonists (e.g., 5-halo-tryptamine compounds or quinoline compounds), serotonin dopamine antagonists (e.g., olanzapine and ziperasidone), monoamine re-uptake inhibitors (e.g., amides), pyridazinone aldose reductase inhibitors (e.g., pyridazinone compounds), serotonergic agents, stimulants of serotonin receptors (e.g., ergoloid mesylate or pergolide mesylate), stimulants of serotonin synthesis (e.g., vitamin B1, vitamin B3, vitamin B6, biotin, S-adenosylmethionine, folic acid, ascorbic acid, magnesium, coenzyme Q10, or piracetam), or serotonin agonists (e.g., fenfluramine).

The first, second, and third agents can also be salts, prodrugs, or solvates of the above-described compounds. A salt can be formed between an anion and a positively charged group (e.g., amino) of an agent. Suitable anions include chloride, bromide, iodide, sulfate, nitrate, phosphate, citrate, methanesulfonate, trifluoroacetate, acetate, chlorophenyoxyacetate, malate, tosylate, tartrate, fumarate, glutamate, glucuronate, lactate, glutarate, benzoate, embonate, glycolate, pamoate, aspartate, parachlorophenoxyisobutyrate, formate, succinate, cyclohexanecarboxylate, hexanoate, octonoate, decanoate, hexadecanoate, octodecanoate, benzenesulphonate, trimethoxybenzoate, paratoluenesulphonate, adamantanecarboxylate, glycoxylate, pyrrolidonecarboxylate, naphthalenesulphonate, 1-glucosephosphate, sulphite, dithionate, and maleate. Likewise, a salt can also be formed between a cation and a negatively charged group (e.g., carboxylate) of an agent. Suitable cations include sodium ion, potassium ion, magnesium ion, calcium ion, and an ammonium cation such as tetramethylammonium ion. The agents also include salts containing quaternary nitrogen atoms. Examples of prodrugs include esters and other pharmaceutically acceptable derivatives, which, upon administration to a subject, are capable of being transformed into active compounds. A solvate refers to a complex formed between an active compound and a pharmaceutically acceptable solvent. Examples of pharmaceutically acceptable solvents include water, ethanol, isopropanol, ethyl acetate, acetic acid, and ethanolamine.

The three active agents mentioned above are known drugs and are readily available to the public. Some can be purchased from chemical companies, such as Sigma-Aldrich, St. Louis, Mo. Regimens for administering these drug compounds are well known and, if necessary, can be easily re-established.

In addition to the three required agents, the composition used in the methods of this invention can include one or more additional active ingredients.

To practice the method of the present invention, an effective amount of the above-described composition can be administered to a subject in need parenterally, orally, buccally, nasally, topically, or rectally. "An effective amount" as used herein refers to the amount of each active agent required to confer a therapeutic effect on the subject, either alone or in combination with one or more other active agents.

Effective doses will vary, as recognized by those skilled in the art, depending on the type or degree of the disorder to be treated; the subject's size, weight, age, and sex; the route of administration; the excipient usage; and the possible co-usage with another therapeutic treatment. The daily dose of the compositions described above can be 5-5,000 mg (e.g., 10-2,500 or 10-3,000 mg) of the first agent, 1-5,000 mg (e.g., 2-1,000 or 2-3,000 mg) of the second agent, and 0.1-1,000 mg (e.g., 1-50 mg) of the third agent.

A subject in need can be identified by a health care professional based on results from a suitable diagnostic method. The term "treating" or "treatment" used herein refers to administering an above-described compositions to a subject, who has a disease mentioned above, a symptom of such a disease, or a predisposition towards such a disease, with the purpose of conferring a therapeutic effect, e.g., to cure, relieve, alter, affect, ameliorate, or prevent the disease, the symptom of it, or the predisposition towards it. The term "reducing fatigue" used herein refers to lessening, ameliorating, or relieving one or more symptoms of fatigue (e.g., low energy, poor endurance, and attention deficits) in a subject. "Reducing aging" refers to lessening, ameliorating, or relieving the deleterious effects of aging (e.g., low vigor, memory loss, weakened vision or hearing, and joint pain) in a subject.

The composition described herein can include a pharmaceutically acceptable carrier to form a pharmaceutical composition. The carrier must be "acceptable" in the sense that it is compatible with the active ingredients of the composition (and preferably, capable of stabilizing the active ingredients) and not deleterious to the subject to be treated. Conventional methods, known to those of ordinary skill in the art of medicine, can be used to administer the pharmaceutical compositions described herein to a subject.

A sterile injectable composition can be a solution or suspension in a non-toxic parenterally acceptable diluent or solvent. The term "parenterally" as used herein refers to subcutaneous, intracutaneous, intravenous, intramuscular, intraarticular, intraarterial, intrasynovial, intrasternal, intrathecal, intralesional, or intracranial injection, as well as any suitable infusion technique. Among the acceptable vehicles and solvents that can be used are mannitol, water, 1,3-butanediol, Ringer's solution, and isotonic sodium chloride solution. In addition, fixed oils are conventionally employed as a solvent or suspending medium (e.g., synthetic mono-or diglycerides). Fatty acids, such as oleic acid and its glyceride derivatives, are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers, which are commonly used in the manufacture of pharmaceutically acceptable solid, liquid, or other dosage forms can also be used for the purpose of formulation.

A composition for oral administration can be any orally acceptable dosage form including capsules, powders, tablets, emulsions and aqueous suspensions, dispersions, and solutions. In the case of tablets or capsules, commonly used carriers or diluents include lactose and corn starch. Lubricating agents, such as magnesium stearate, can be added. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition for topical administration can be prepared in the form of an ointment, a gel, a plaster, an emulsion, a lotion, a foam, a cream of a mixed phase or amphiphilic emulsion system (oil/water-water/oil mixed phase), a liposome, a transfersome, a paste, or a powder.

Any of the compositions described above can also be administered in the form of suppositories for rectal administration. It can also be designed so that the composition is released in the intestine. For example, the composition is confined in a solid sub-unit or a capsule compartment that has a matrix or a wall or a closure comprising an enteric polymer which dissolves or disperses at the pH of the small or large intestine to release the drug substance in the intestine. Suitable enteric polymers have been described above and also in U.S. Pat. No. 5,705,189.

A composition can be included in a drink or food product. Examples include tea (e.g., a tea drink and the contents of a tea bag), soft drinks, juice (e.g., a fruit extract and a juice drink), milk, coffee, cookies, cereals, candies, and snack bars.

The compositions described above can be preliminarily screened for their efficacy in treating an above-described disease or disorder by an in vitro assay and then confirmed by animal experiments and clinical trials. Other methods will also be apparent to those of ordinary skill in the art.

Without further elaboration, it is believed that one skilled in the art can, based on the description herein, utilize the present invention to its fullest extent. All of the publications cited herein (including patents and patent applications) are incorporated by reference in their entirety.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method for treating McArdle disease, comprising administering to a subject in need thereof an effective amount of a composition containing:
    a first agent that is an adenosine 5'-monophosphate-activated protein kinase (AMPK) activator;
    a second agent that possesses anti-inflammatory activity; and
    a third agent that possesses or maintains serotonin activity.

2. The method of claim 1, wherein the AMPK activator is selected from the group consisting of metformin, phenformin, buformin, 5-aminoimidazole-4-carboxamide ribonucleoside, thienopyridones, resveratrol, nootkatone, thiazole, and adiponectin.

3. The method of claim 1, wherein the first agent is metformin, phenformin, buformin, ephedrine, thyroxine, salicylanilide, or salicylic acid.

4. The method of claim 3, wherein the first agent is metformin hydrochloride.

5. The method of claim 1, wherein the second agent is a non-steroidal anti-inflammatory compound.

6. The method of claim 1, wherein the second agent is aspirin, diclofenac, ibuprofen, indomethacin, acetaminophen, nimesulide, or a COX-2 inhibitor.

7. The method of claim 6, wherein the second agent is aspirin.

8. The method of claim 1, wherein the third agent is serotonin or a serotonin re-uptake inhibitor.

9. The method of claim 8, wherein the third agent is serotonin sulfate, a serotonin creatinine sulfate complex, or serotonin hydrochloride.

10. The method of claim 1, wherein the composition contains 5-5,000 mg of the first agent, 1-5,000 mg of the second agent, and 0.1-1,000 mg of the third agent.

11. The method of claim 10, wherein the composition contains 5-1,500 mg of the first agent, 1-1,000 mg of the second agent, and 0.1-100 mg of the third agent.

12. The method of claim 11, wherein the composition contains 5-1,000 mg of the first agent, 1-500 mg of the second agent, and 0.1-50 mg of the third agent.

13. The method of claim 1, wherein the composition contains metformin hydrochloride, aspirin, and a serotonin creatinine sulfate complex.

14. The method of claim 13, wherein the composition contains 5-5,000 mg of metformin hydrochloride, 1-5,000 mg of aspirin, and 0.1-1,000 mg of the serotonin creatinine sulfate complex.

15. The method of claim 14, wherein the composition contains 5-1,500 mg of metformin hydrochloride, 1-1,000 mg of aspirin, and 0.1-100 mg of the serotonin creatinine sulfate complex.

16. The method of claim 15, wherein the composition contains 5-1,000 mg of metformin hydrochloride, 1-500 mg of aspirin, and 0.1-50 mg of the serotonin creatinine sulfate complex.

17. The method of claim 1, wherein the composition further comprises a pharmaceutically acceptable carrier.

18. The method of claim 1, wherein the composition contains the first, second, and third agents as the only active ingredients.

* * * * *

UNITED STATES PATENT AND TRADEMARK OFFICE
CERTIFICATE OF CORRECTION

PATENT NO. : 8,377,947 B2
APPLICATION NO. : 12/723771
DATED : February 19, 2013
INVENTOR(S) : Chien-Hung Chen Page 1 of 1

It is certified that error appears in the above-identified patent and that said Letters Patent is hereby corrected as shown below:

<u>Title Page, Col. 2 (Other Publications)</u>
Line 25, Delete "Presure" and insert -- Pressure -- therefor.

Line 27, Delete "ofAMP" and insert -- of AMP -- therefor.

<u>In the Claims</u>

<u>Column 6</u>
Line 65, In Claim 2, delete "5-aminoimidazole -4-carboxamide" and insert
-- 5-aminoimidazole-4-carboxamide -- therefor.

Signed and Sealed this
Twenty-eighth Day of May, 2013

Teresa Stanek Rea
*Acting Director of the United States Patent and Trademark Office*